United States Patent [19]

Frawley

[11] Patent Number: 4,895,833
[45] Date of Patent: Jan. 23, 1990

[54] LIVER LACTOGENIC FACTOR

[75] Inventor: L. Stephen Frawley, Charleston, S.C.

[73] Assignee: The Medical University of South Carolina, Charleston, S.C.

[21] Appl. No.: 22,893

[22] Filed: Mar. 6, 1987

[51] Int. Cl.[4] .................... A61K 37/02; A61K 35/14; A61K 35/407; C07K 15/06
[52] U.S. Cl. ........................................ 514/2; 514/21; 530/300; 530/399; 530/846; 424/101; 424/106
[58] Field of Search .................... 424/106, 101; 514/2, 514/21; 530/846, 300, 399

[56] References Cited

U.S. PATENT DOCUMENTS 2,370,154  2/1945  Fleischer et al. .................... 424/106

OTHER PUBLICATIONS

Errick, J. E. et al., In: *Lactation Physiology, Nutrition and Breast-Feeding*, (Neville, M.C., et al., eds.) Plenum Publ., N.Y., pp. 179–196 (1983).
Nicholas, K. R., et al., *Biochem. Biophys. Res. Commun.*, 94:1424–1431 (1980).
Neville, M.C. et al., In: *Lactation Physiology, Nutrition and Breast-Feeding*, (Neville, M.C. et al., eds.) Plenum Publ., N.Y., pp. 141–177 (1983).
Anderson, T. R. et al., *Gen. Comp. Endocrinol.* 54:236(1984).
Mick, C. C. W. et al., *Endocrinol.* 116:2049–2053 (1985).
Nicoll, C. S. et al., *Endocrinol.* 116:1449–1453 (1985).
Del Pozo, E. et al., *Horm. Pres.* 10:143–172(1979).
Emerman, J. T. et al., *In Vitro* 13:316–328 (1977).
Topper, Y. T. et al., *Physiol. Rev.* 60:1049–1106 (1980).
Rosen, J. M., et al., *Recent Prog. Horm. Res.* 36:157–193 (1980).
Kyriakou, S. Y., et al., *J. Endocrinol.* 59:199–200 (1973).
Lyons, W. R., *Proc R. Soc. London Ser. B.* 149:303–325 (1958).
Falconer, I. R., *Aust. J. Biol. Sci.*, 33:71–84 (1980).
Strong, C. R. et al., *Biochem. J.* 128:1303–1308 (1972).
Jones, E. A. et al., *Biochem. J.* 130:997–1002 (1972).
Frawley, L. S. et al., *Endocrinol.* 119:2867–2869 (1986).
Kaetzel. C. S. et al., *J. Dairy Sci.* 67:64 (1984).
Vaitukaitis, J., et al., *J. Clin. Endocrinol. Metab. 33:988 (1971).*
Boockfor, F. R. et al., *Neuroendocrinol.* 42:64 (1986).
Mittra, et al., *Biochem. Biophys. Res. Commun.* 95:1750–1767 (1980).

*Primary Examiner*—Jacqueline M. Stone
*Attorney, Agent, or Firm*—Needle & Rosenberg

[57] ABSTRACT

The present invention relates to liver lactogenic factor and to its isolation, purification and characterization. The liver lactogenic factor of the present invention is useful to increase milk and/or casein production in lactating female mammals. The invention additionally pertains to a novel bioassay capable of identifying lactogenic factors.

7 Claims, 6 Drawing Sheets

LIVER LACTOGENIC FACTOR

FIELD OF THE INVENTION

The invention pertains to liver lactogenic factor, a polypeptide which is capable of augmenting milk production in mammals, and to compositions containing same. The invention further pertains to an assay for identifying other lactogenic factors and to processes for isolating these other factors.

BACKGROUND OF THE INVENTION

I. In Vitro Assays for Lactogenic Factors

The extreme complexity of the mammalian hormone environment has made in vitro culture techniques indispensable in elucidating the role of hormones in mammary cell function. Model systems for the study of mammary hormonal control are reviewed by Errick, J.E., et al. ("In Vitro Model Systems for the Study of Hormonal Control of Mammary Gland Growth and Differentiation, in: *Lactation Physiology, Nutrition, and Breast-Feeding* (Neville, M. C., et al., eds., Plenum Publishing, New York (1983), pp. 179–196)), which reference is hereby incorporated in its entirety. Such systems have been found to be useful in deducing whether a particular factor has an effect on mammary cell function (i.e., lactogenesis, lactation, mammatogenesis, etc.)

One major in vitro model system for the study of hormonal control involves the culture of small pieces of mammary tissue containing a mixture of epithelial cells and stromal cells. Lactogenesis may be assayed, in such ex plante cultures, by measuring the amount of alpha-lactalbumin, a component of the lactose synthetase enzyme, a well-known marker of mammary differentiation, and correlating the amount of alpha-lactalbumin with the extent of lactogenesis (Nicholas, K.R., et al., *Biochem. Biophys. Res. Commun.* 94:1424–1431 (1980)). Lactogenesis may also be assayed by measuring any characteristic indicator of milk synthesis such as casein synthesis, casein mRNA, lactose, etc.

II. Hormones and Factors Which Control Lactation and Lactogenesis

Several hormones and factors have been found to regulate mammary growth, lactation and lactogenesis. Among the most important of the lactogenic hormones are the somatomammotropic hormones. These hormones are a group of single-chain polypeptides having molecular weights of between 21,000–23,000 that include two hormones of pituitary origin, prolactin and growth hormone, and one hormone synthesized by the syncytiotrophoblast layers of the placenta, placental lactogen. All three hormones have varying degrees of lactogenic activity, however, prolactin is thought to play the major role in the regulation of mammary function (Neville, M.C., et al., "Cellular and Molecular Aspects of Hormonal Control," in: *Lactation Physiology, Nutrition, and Breast-Feeding* (Neville, M. C., et al., eds., Plenum Publishing, New York (1983), pp. 141–177, which reference is hereby incorporated in its entirety)). Prolactin is involved in the regulation of the activity of the mammary gland, stimulates milk production, and stimulates mammary growth and differentiation.

Prolactin also is capable of stimulating the growth of various target organs, such as the crop sac of pigeons (Anderson, T. R., et al. *Gen. Como. Endocrinol.* 54:236 (1984). It has been found to directly stimulate liver cells to secrete a factor, termed "synlactin," which acts synergistically with the hormone to promote the growth of pigeon crop sac (Mick, C. C. W., et al. *Endocrinol.* 116:2049–2053 (1985), Nicoll, C. S., et al., *Endocrinol.* 116:1449–1453 (1985)). At present, synlactin has no known role in lactation or lactogenesis.

Several hormones and factors control prolactin expression. Prolactin inhibitor factor, which is produced in the hypothalamus (Del Pozo, E., et al., *Horm. Res.* 10:143–172 (1979)) controls prolactin release. D-opamine is believed to inhibit prolactin secretion, and drugs such as L-dopa, which is converted to dopamine, and bromocryptine, a dopamine agonist, have also been found to interfere with prolactin release. In contrast, estrogens have been found to increase both pituitary and plasma prolactin levels (Emerman, J. T., et al., *In Vitro* 13:316–328 (1977)).

Placental lactogen, also known as human chorionic somatomammotropin (hCS), is secreted only during pregnancy. Thus, its physiological role in mammary function is limited to the stimulation of mammary growth and differentiation, and not to the secretion of milk.

Several additional factors and hormones have also been found to effect lactation. Glucocorticoids have been found to enhance both prolactin-induced differentiation of mammary tissue, and casein production (Topper, Y. J., et al., *Physiol. Rev.* 60:1049–1106 (1980)). Progesterone has been found to inhibit prolactin-induced effects (Rosen, J. M., et al., *Recent Proo. Horm. Res.* 36:157–193 (1980)). Specifically, progesterone has been found to prevent those changes which lead to terminal differentiation and milk secretion in the mammary gland (Neville, M. C., et al., 1983).

Although the major metabolic role of insulin involves the regulation of serum glucose concentration, insulin is believed to play a role in the development of the mammary glands. However, since lactogenesis occurs after parturition in severely diabetic rats, insulin probably does not play a regulatory role in lactogenesis (Kyriakou, S. Y., et al., *J. Endocrinol.* 59:199–200 (1973)).

Several thyroid hormones have been found to promote mammary growth and lactation but are not believed to regulate lactogenesis (Lyons, W. R., *Proc. R. Soc. London, Ser. B.* 149:303–325 (1958)). Prostaglandins have also been implicated as playing a possible role in the regulation of mammary function; however, due to conflicting reports of prosta-glandin-related effects, the precise role of prostaglandins in lactogenesis is unclear (Neville, M. C., et al. (1983)).

In summary, several different bioassys have been developed which are capable of identifying lactogenic factors. Using such assays, several hormones and factors have been identified as having a significant regulatory role in lactogenesis and lactation. The ability of the above described bioassays to identify novel lactogenic factors is limited by the sensitivity of existing assays. Thus, desired potent lactogenic factors may escape detection if they are present at low concentrations in a tissue sample. However, a need exists for more sensitive bioassays for lactogenic factors if additional lactogenic factors are to be discovered.

SUMMARY OF THE INVENTION

The present invention relates to a lactogenic factor found in liver tissue (liver lactogenic factor), and to pharmacological compositions containing same, which are capable of stimulating casein release, and of augmenting milk production. The invention further relates to processes for isolating said factor and methods for its use.

The invention further relates to a method for determining the presence of a lactogenic factor in a sample, the method comprising assaying for the presence of the factor in the sample using a reverse hemolytic plaque bioassay.

Additionally, the invention pertains to methods for augmenting the production of milk or of casein in milk which comprises providing to a recipient lactating mammal an effective amount of said liver lactogenic factor.

DESCRIPTION OF THE PREFERRED EMBODIMENTS

Figure 1:
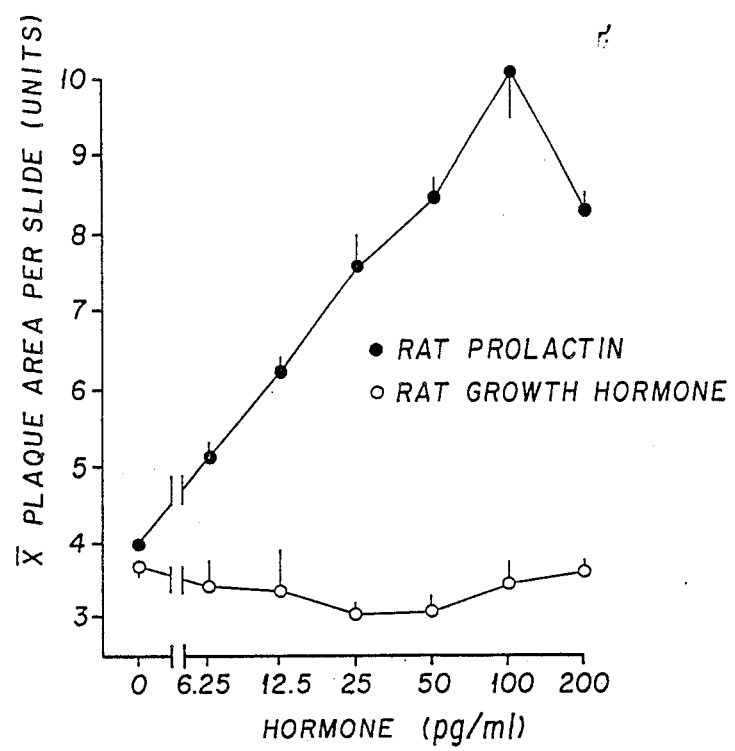
FIG. 1 shows dose response curves for casein plaque formation by mammary cells treated with rat prolactin (PRL) or rat growth hormone (GH) (NIADDK-B5 and -B9, respectively). Values are mean ± standard error (SE) of triplicate determinations within a single assay and are representative of two additional assays.

As used herein, the term "factor" refer to chemical compounds such as hormones, vitamins, peptides, and molecules which may be recognized by cellular receptor molecules.

For the purposes of the present invention, a factor is said to be "lactogenic" if it is capable of stimulating a female mammal to produce either (1) enhanced levels of milk, or (2) milk having a higher nutritional value (for example, by increasing the casein content of the milk).

By the term "liver lactogenic factor" is intended the naturally occurring polypeptide isolated by the technique described below and polypeptides which are substantially similar thereto, whether synthetic or naturally occurring. A factor is said to be "substantially similar" to another factor if it is capable of performing substantially the same function, and has substantially the same chemical structure. Thus the term is intended to include those polypeptides synthesized using, for example, a Merrifield synthesis, and those polypeptides produced using recombinant technology. The term further includes polypeptides which are substantially the same as the naturally occurring polypeptide but which differ therefrom by one or more amino acids while still having substantially the same biological activity. The liver lactogenic factor isolated by the procedure described below is characterized as follows. This factor is believed to be a protein having a molecular weight of approximately 9,400 daltons. The liver lactogenic factor may be purified into a substantially pure form by means which are commonly known in the art of peptide purification. Such means include HPLC chromatography, gel filtration, electrophoresis, affinity chromatography, etc., using the casein plaque bioassay as a purification guide.

The liver lactogenic factor may be obtained from mammalian liver tissue. To isolate such a factor from tissue, thin slices of the tissue (preferably 0.3–0.5 mm thick, approximately 1.0 g) are prepared. Any means of preparing such tissue slices may be employed. One preferred means employs a Statie-Riggs hand microtome according to the method of Nicoll, C. S., et al. (*Endocrinol.* 116:1449 (1985)). The sliced tissue is then incubated in a suitable cell culture medium. Although any such medium may be employed, one preferred medium is Dulbecco's Modified Eagle's Medium which has been supplemented with 0.1% bovine serum albumin and antibiotic (such as penicillin, (100 U/ml) streptomycin (100 ug/ml), etc.) to control against bacterial contamination. Examples of other suitable cell culture media are described in Lambert, K. J., et al., *Animal Cell Biotechnology,* Vol. 1, Academic Press, 1985, pp. 86–122. The tissue is, preferably, incubated with constant slow stirring (using an impeller bar which is placed above the slices) for between 1–20 hours, preferably 1.5 hours, at an incubation temperature of approximately 37° C. in an atmosphere of 95% air:5% carbon dioxide. At the end of the incubation period, the culture medium is filtered, i.e., by filtration through Whatman No. 1 filter paper (Whatman Ltd., Maidstone, England) and the filtrate is analyzed for the presence of a lactogenic factor.

In order to determine whether a sample contains a lactogenic factor, a variety of different assays may be employed (Falconer, I. R., *Aust. J. Biol. Sci.* 33:71–84 (1980)). For example, it is possible to assay for the presence of a lactogenic factor using any characteristic biochemical indicator of milk synthesis. Such assays include measurements of the synthesis of medium-chain fatty acids (Strong, C. R., et al., *Biochem. J.* 128:1303–1308 (1972)), measurements of casein concentration (Rillema, J. A., et al., *Endocrinol.* 100:529–536 (1977)), measurements of casein mRNA (Devinoy, E., et al., *Biochem. Bioohvs. Acta.* 517:360–366 (1978); Matusik, R. J., et al., *J. Biol. Chem.* 253:2343–2347 (1978)), or measurements of lactos (Joes, E. A., et al., *Biochem. J.* 130:997–1002 (1972)). It is, however, preferable to employ the novel bioassay of the presett invention.

One aspect of the present invention is the discovery of a novel, in vitro bioassay capable of identifying lactogenic factors. This bioassay which measures the amount of casein released from isolated mammary cells, employs a reverse hemolytic plaque assay. This assay was described by Frawley, L. S., et al., *Endocrinol.* 119:2867–2869 (1986), which reference is hereby incorporated by reference in its entirety. This novel assay is sensitive enough to measure the biopotency of prolactin (a lactogenic factor) released from a single pituitary cell, and can be used to evaluate both the biopotency and immunopotency of hormone released from such cells.

To perform the assay, approximately 5.0 g of tissue are dissected aseptically from the lower abdomal mammary glands of lactating (days 9–11) rats which have been maintained with their litters until the time of sacrifice. The tissue is then diced, as with scalpel blades, into 2–4 mm$^3$ fragments. The tissue fragments are then transferred to a container such as a spinner flask containing a protease (preferably collagenase) (1 mg/ml) in approximately 20 ml of culture medium (Dulbecco's Modified Eagle's Medium containing 0.1% bovine serum albumin, penicillin G and streptomycin sulfate (MEM)) and incubated with continuous stirring for 0.5–2 hours at approximately 37° C. The collagenase is preferably type III collagenase (Cooper Biomedical, Malverne, PA). The tissue fragments are taken up and expelled through the tip of a 5 ml pipette at the midpoint and conclusion of the incubation. The cells and tissue fragments are then pelleted by centrifugation ($700 \times g$ for 15 minutes), resuspended in minimal essential medium containing the albumin and antibiotics described above (MEM) and passed successively through two sterile pieces of Nitex nylon screening (75 um mesh, Tetko Inc., Elmsford, N.Y.). The filtered cells are centrifuged again ($500 \times g$, for 10 minutes), resuspended in MEM, and passed through two successive sterile pieces of Nitex screening (25 um mesh) to yield a suspension in which 70–80% of the cells are monodispersed.

Rat casein was isolated from rat whole milk by the differential extraction procedure of Kaetzel, C.S., et al. (*J. Dairy Sci.* 67:64 (1984)). The purity of the material was assessed by running it in tandem with molecular weight markers on a sodium dodecyl sulfate-Laemmli gel (15%) followed by scanning densitometry. When subjected to electrophoresis, this casein preparation separated into three distinct bands that corresponded closely to those described as alpha, beta, and gamma caseins in rat milk (Kaetzel, C. S., et al.). Antisera for use in plaque assays was prepared by injecting this casein preparation into rabbits according to the multiple site procedure of Vaitukaitis, J., et al. (*J. Clin. Endocrinol. Metab.* 33:988 (1971)).

The plaque assay for casein release from mammary cells is performed by mixing a suspension of monodispersed mammary cells, preferably at a concentration of between $2 \times 10^5 \times 5 \times 10^5$ cells per ml, in cell culture medium with an equal volume of protein A-coated ovine erythrocytes (oRBCs, 12%) and then by infusing this mixture into a chamber. The chamber may, for example, be constructed by affixing a glass cover slip to a poly-L-lysine-coated glass microscope slide by two pieces of double-sided adhesive tape (Boockfor, F. R., et al., *Neuroendocrinol.* 42:64 (1986), which reference is hereby incorporated in its entirety). The cells are then allowed to attach as a monolayer during a preincubation (30–60 minutes in length), thereby forming an assay chamber. The assay chambers are then washed, filled with either medium alone or test samples, and placed overnight in a humidified incubator at 37° C. with an atmosphere of 95% air : 5% carbon dioxide. Between 15–20 hours later, the assay chambers are washed with fresh medium and incubated with casein antibody (diluted 1:500) for approximately 2 hours. Plaque development is completed during a subsequent incubation (approximately 50 minutes) with guinea pig complement (diluted 1:60). The monolayers are then fixed and stained with toluidine blue (Boockfor, F. R., et al. (1986)) prior to microscopic quantification of plaque formation.

The reverse hemolytic plaque assay for lactogenic factors may be performed on cells from any tissue source. Thus, for example, pituitary cells or liver cells may be assayed for their ability to produce lactogenic factors.

The above-described casein plaque assay may be performed on individual cells in microwells. To accomplish this, approximately 170 ul of culture medium containing (on average) a single cell is added to each culture well of a microtiter plate and incubated for approximately 14 hours under the same conditions as described above. A 150 ul volume is then removed and either immediately assayed or stored frozen for subsequent analysis. 50 ul volume of antisera (appropriately diluted, if necessary) in assay medium containing oRBCs (0.125%) is then added. Approximately two hours later the monolayers may be exposed to guinea pig complement (preferably 50 ul of a 1:50 dilution) for approximately one hour and then fixed and stained with toluidine blue, as described above, prior to microscopic quantification of plaque formation.

The presence of a lactogenic factor is revealed by determining the percentage of plaque-forming cells, and the average size of the plaques that are formed. Each of these variables increases with increasing lactogenic factor concentration. By calculating the average plaque area per incubation slide, which is simply the product of these two variables, it is possible to quantify the cumulative response of mammary cells to lactogenic factors.

Included within the scope of the present invention are those peptide fragments of liver lactogenic factor which are capable of functioning as lactogenic factors. Included as well are the use of additional amino acid residues added to enhance coupling to carrier protein or amino acid residues added to enhance the lactogenic effect. The amino acid residues of liver lactogenic factor may be in their protected or unprotected form, using appropriate amino or carboxyl protecting groups as is known in the art. The liver lactogenic factor may also be in the presence of cationic salt groups. Useful cations are alkali or alkaline earth metallic cations (i.e., Na, K, Li, ½Ca, ½Ba, etc.) or amine cations (i.e., tetraalkylammonium, trialkylammonium, where alkyl can be $C_1$-$C_{12}$).

The invention further pertains to polypeptides that, in addition to containing the amino acid sequence of liver lactogenic factor, may contain or lack one or more amino acids that may not be present in the naturally-occurring sequence, wherein such polypeptides are functionally similar to the chosen polypeptide. Such polypeptides for the present invention, are termed "functional derivatives," provided that they demonstrate activity which is substantially similar to that of liver lactogenic factor.

The liver lactogenic factor may be in the form of the free amines (on the N-terminus), or acid-addition salts thereof. Common addition salts are hydrohalic acid salts, i.e., HBr, HI, or more preferably, HCl.

The liver lactogenic factor-containing compositions of the present invention can be formulated according to known methods to prepare pharmaceutically useful compositions, whereby liver lactogenic factor or its functional derivatives are combined in admixture with a pharmaceutically acceptable carrier vehicle. Suitable vehicles and their formulation, inclusive of other human proteins, e.g., human serum albumin, are described for example in *Remington's Pharmaceutical Sciences* (16th Ed. A. Oslo Ed. Mack, Easton, Pa. (1980)). In order to form a pharmaceutically acceptable composition suitable for effective administration, such compositions will contain an effective amount of the liver lactogenic factor, or its functional derivatives, together with a suitable amount of carrier vehicle.

An "effective amount" of liver lactogenic factor is one which is sufficient to enhance either casein production or milk production in a lactating mammal. The effective amount may vary depending upon criteria such as the age, weight, physical condition, past medical history, and sensitivity of the recipient.

Compositions containing liver lactogenic factor or its functional derivatives may be administered orally, intravenously, intramuscularly, subcutaneously, or locally.

For the purpose of parental administration, compositions containing liver lactogenic factor may be dissolved in distilled water and the pH-value adjusted to about 6 to 8. In order to facilitate the lyophilization process resulting in a suitable product, lactose could be added to the solution. The solution is then filter sterilized, introduced into vials, and lyophilized. The concentration of liver lactogenic factor in these compositions may vary from $10^{-12}$M to $10^{-5}$M.

Additional pharmaceutical methods may be employed to control the duration of action. Controlled release preparations may be achieved by the use of polymers to complex or adsorb liver lactogenic factor or its functional derivatives. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release Another possible method to control the duration of action by controlled release preparations is to incorporate liver lactogenic factor into particles of a polymeric material such as polyesters, polyamino acids, hydrogels, poly (lactic acid) or ethylene vinylacetate copolymers. Alternatively, instead of incorporating liver lactogenic factor into these polymeric particles, it is possible to entrap liver lactogenic factor in microcapsules prepared, for example, by coacervation techniques or by interfacial polymerization, for example, hydroxylmethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences, supra* (1980).

The liver lactogenic factor of the present invention and its functional derivatives, either alone or in pharmacologically acceptable compositions are useful for enhancing lactation in female mammals. Administration of liver lactogenic factor results in an increase in milk production and in the concentration of casein present in milk. The invention, therefore, has utility in augmenting milk, cheese, etc. production in the dairy industry. Additionally, the invention may have utility for nursing women who are in need of higher quantity or quality milk.

Having now generally described this invention, the same will be better understood by reference to certain specific examples which are included herein for purposes of illustration only and are not intended to be limiting of the invention, unless specified.

EXAMPLES

EXAMPLE 1

USE OF THE REVERSE HEMOLYTIC PLAQUE ASSAY TO MEASURE PROLACTIN CONCENTRATION

The reverse hemolytic plaque asay was used to measure prolactin from pituitary cells according to the method described above. 170 ul of culture medium containing (on average) a single pituitary cell was inoculated into microtiter plates and incubated for 14 hours as described previously. A 150 ul volume was then removed and replaced with a 50 ul volume of rabbit anti-rat prolactin serum (diluted 1:125) in MEM containing ovine sheep red blood cells. Varying concentrations (from 0 pg/ml–400 pg/ml) of prolactin were added to the culture medium, and the effect on plaque formation and plaque area was determined. Two hours later, the monolayers were exposed to guinea pig complement (50 ul of 1:50) for 50 minutes and then fixed as described above. The results of this experiment are shown in Table 1.

TABLE 1

Effect of rat prolactin (rPRL) on casein plaque development. Results are mean ± SE of 7 separate experiments

| rPRL (pg/ml) | A % PFC | B mean plaque area ($u^2 \times 10^{-3}$) | C mean plaque area per slide (A × B) |
|---|---|---|---|
| 0 | 17.6 ± 1.4 | 19.4 ± 2.9 | 3.31 ± 0.4 |
| 6.25 | 20.6 ± 1.4 | 21.7 ± 2.3 | 4.44 ± 0.4 |
| 12.5 | 22.6 ± 1.1 | 22.7 ± 2.4 | 5.07 ± 0.4 |
| 25.0 | 24.5 ± 1.3 | 25.0 ± 2.9 | 6.03 ± 0.5 |
| 50.0 | 26.1 ± 1.2 | 27.4 ± 2.9 | 7.06 ± 0.6 |
| 100 | 28.2 ± 1.2 | 30.8 ± 3.5 | 8.55 ± 0.8 |
| 200 | 26.5 ± 1.0 | 28.8 ± 3.0 | 7.50 ± 0.7 |
| 400 | 26.8 ± 1.5 | 29.4 ± 3.2 | 7.78 ± 1.0 |

Treatment with graded doses of prolactin during the preincubation period increased (to approximately the same degree) both the percentage of plaque-forming cells and the average size of plaques that formed. Each of these variables exhibited a dose-related increase between 6.25 and 100 pg/ml of prolactin and a slight depression in response to higher concentrations. This depression may be due to a desensitization or down-regulation of the response.

FIG. 1 summarizes the results obtained in a single representative experiment and illustrates the specificity and sensitivity of the plaque assay. Treatment with rat prolactin increased, in a dose-related manner, the average plaque area per slide, whereas identical concentration of rat gonadotrophin had no effect. Neither gonadotrophin, leutinizing hormone, follicle-stimulating hormone, nor thyroid-stimulating hormone were capable of inducing plaque formation, even in doses as high as 10 mg/ml. The exquisite sensitivity of the assay is evidenced by the different responses ($P<0.01$, Student's t test) elicited by 0 and 6.25 pg/ml doses of prolactin. When corrected for the volume of incubation chamber (25 ul), this 6.25 pg/ml translates into 156 fg of prolactin.

Figure 2A:
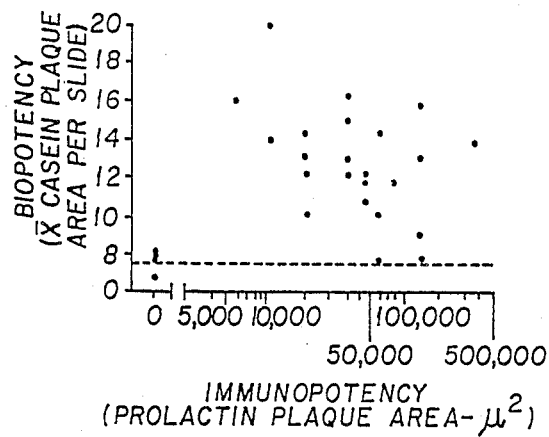
FIG. 2 shows a comparison of bio- and immunopotency of PRL released from the same pituitary cells. Medium bathing individual pituitary cells for 14 h was removed for evaluation of biopotency. The same cell was then subjected to a prolactin (PRL) plaque assay to measure the release of immunoreactive hormone. Each panel shows the results of a separate experiment and each point reflects a single measurement in the PRL plaque assay and duplicate determinations (60-ul volumes were used to flush and fill chambers) in the casein plaque bioassay. Values for individual cells that did not form PRL plaques are plotted on the extreme left of the abscissa and the average of these for each experiment is denoted by the dashed line.
Figure 2B:
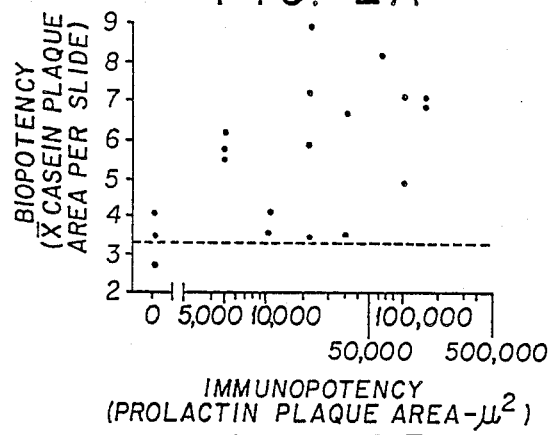
Figure 2C:
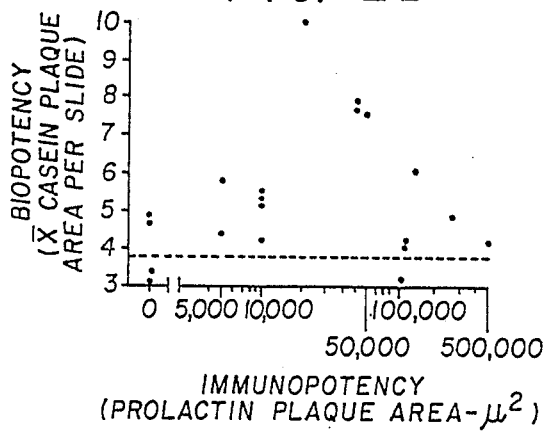

FIG. 2 shows the results of three separate experiments in which the biopotency and immunopotency of prolactin released in the same cells are measured. Media samples taken from individual pituitary cells that did not form prolactin plaques exhibited biopotencies which were relatively low. In contrast, unequivocal bioactivity was detected in media samples from most pituitary cells that released immunoreacted prolactin. A relationship between the bioactivity and immunoreactivity of hormones released from the same cells was not apparent.

EXAMPLE 2

STIMULATION OF CASEIN RELEASE BY LIVER LACTOGENIC FACTOR

The reverse hemolytic plaque assay, described above, was used to measure casein release from individual rat mammary cells in culture. Mammary cells were isolated from mammary tissue as described above. Assay chambers containing monolayers of mammary cells (from day 10 lactaters) and indicator ovine red blood cells, were preincubated for 17 hours and then subjected to the casein plaque assay. Addition of 25 or 100 pg/ml rat prolactin (rPRL) at the beginning of the preincubation period increased the percentages of all mammary cells that released casein from a control value of 19.4 to 23.5 and 32.9, respectively. In contrast, addition of medium that had bathed liver slices (for three hours) from day 12 lactaters had no effect. Treatment with prolactin, or with medium containing liver lactogenic factor (diluted 1:32) increased the average size of the plaques that formed. The results of this experiment are shown in Table 2.

TABLE 2

| Stimulation of casein production in mammary cells by liver lactogenic factor. | | | |
|---|---|---|---|
| MEDIUM | 0 pg/ml rRPL | 25 pg/ml rRPL | 100 pg/ml rRPL |
| Control | 18.8 ± 1.3 | 32.7 ± 3.1 | 40.8 ± 1.4 |
| Liver | 60.8 ± 1.6 | 76.7 ± 5.0 | |

Surprisingly, medium bathing liver slices from lactaters (and thus containing the liver lactogenic factor) was far more potent than rat prolactin in stimulating casein release. Moreover, the combined effects of prolactin and liver lactogenic factor were additive rather than synergistic. Incubations of kidney tissues from lactating rats, liver tissue from male or virgin female rats, and insulin-like Growth Factor-1 (IGF-1) had no activity in the above assay systems. These results demonstrate that liver tissue from lactating rats contained a factor (liver lactogenic factor) which actually mimicked the action of prolactin. Liver lactogenic factor increased the amount of casein released from mammary cells but did not increase the number of cells committed to casein release.

EXAMPLE 3

CHARACTERIZATION OF LIVER LACTOGENIC FACTOR

Slices of the liver tissue (0.3–0.5 mm thick, approximately 1.0 g) were prepared as described above. The slices were incubated in culture medium, as described previously, and the medium was filtered through Whatman No. 1 filter paper.

The possibility that the filtrate contained a lactogenic activity was investigated using the casein plaque bioassay system described previously. Assay incubation chambers containing monolayers, mammary cells, and ovine red blood cells were preincubated for 17 hours in the presence or absence of liver incubation medium, either alone or in combination with rat prolactin. The chambers were then flushed with fresh medium and incubated with rabbit anti-rat casein serum (1:500) for two hours. Plaques were developed using a subsequent 50-minute incubation with a 1:60 dilution of guinea pig serum (a source of complement). After staining with toluidine blue, plaque development was quantified (with the aid of a microscope) by determining the percentage of cells that formed plaques or the sizes of plaques that developed. Statistical significance of differences between treatment groups was determined by the Student's Test (Steel, R. J. B., et al., *Principles and Procedures of Statistics*, McGraw Hill, New York, 1980, page 114.)

Figure 3:
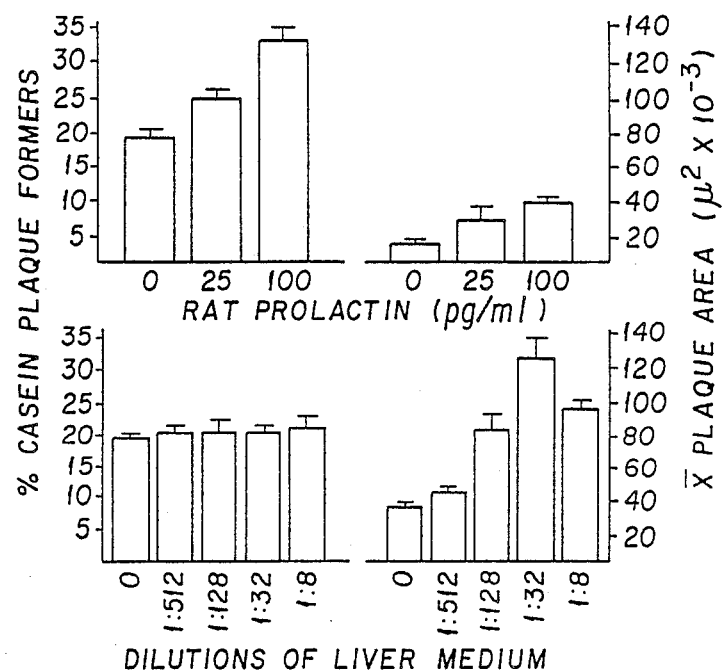
FIG. 3 shows the differential effects of rat prolactin and liver incubation medium (containing liver lactogenic factor) on casein plaque development. Monolayers of rat mammary cells and ovine red blood cells (oRBCs) were first exposed for 17 h to graded doses of rat PRL or serial dilutions of liver incubation medium and then subjected to a casein plaque assay. Both the percent of plaque forming colonies (PFC) and the sizes of plaques that developed were quantified on the same monolayers. Rat PRL had a stimulatory influence on each of these variables whereas liver medium augmented only plaque size. In this and the following figure, results are presented as the mean ± SE of triplicate determinations in a single experiment which is representative of at least 3 separate experiments.

FIG. 3 shows a comparison of the quantitative effects of liver incubation medium (which contained liver lactogenic factor) and rat prolactin on two variables of casein plaque development. Treatment with rat prolactin evoked dosetrelated increases in both the percentage of mammary cells that formed plaques and the average size of plaques that developed. In contrast, dilutions of liver lactogenic factor had absolutely no effect on the proportion of casein plaque formers that caused graded increases in average plaque area. In fact, maximally effective dilutions of liver lactogenic factor were much more potent than comparable doses of prolactin when only the relative amount of casein released per cell (plaque size) was considered. Incubation medium that bathed kidney tissue from lactating rats and liver tissue from male or virgin female rats, as well as insulinlike growth factor-I, were all tested and found to have no activity in this assay system.

Figure 4:
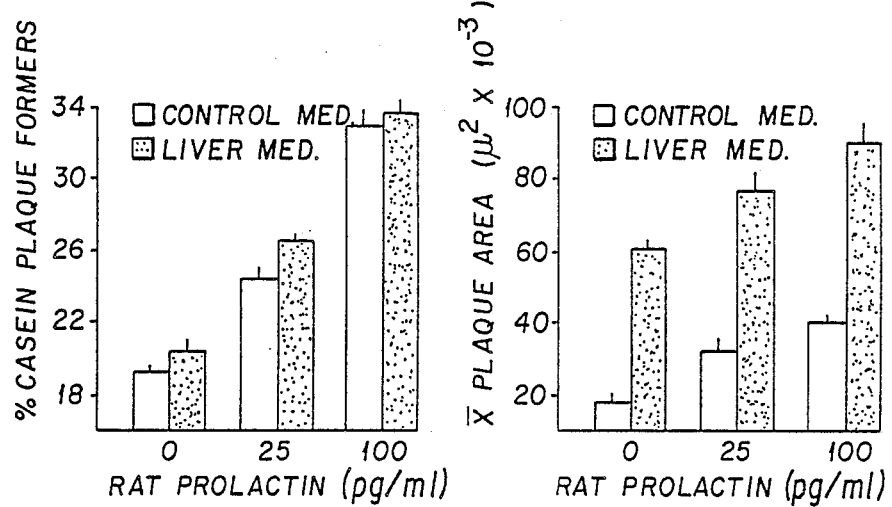
FIG. 4 shows interactions of rat PRL and liver incubation medium containing liver lactogenic factor (1:32, a maximally effective dilution) on casein plaque development. Control medium consisted of Dulbecco's Modified Eagle's Medium containing 0.1% BSA and antibiotics. The effects of control medium alone, or liver medium only, are represented as 0 pg/ml rat prolactin.

The combined effects of rat prolactin and liver lactogenic factor are illustrated in FIG. 4. Coincubation with liver medium from lactators did not alter the effect of prolactin on the percentage of casein plaque formers. Conversely, plaque size was augmented by combined treatments, and this interaction appeared to be additive. Thus, liver lactogenic factor only partially mimicked the action of prolactin; it increased the amount of casein released per mămmary cell without affecting the number of cells committed to casein release. Because the presence of the liver lactogenic factor was associated with a physiologic state of elevated prolactin secretion (lactation), one possibility which may be proposed was that liver lactogenic factor served as an extracellular mediator of prolactin's action. The existence of such a liver lactogenic factor might provide a mechanism by which the lactogenic and mammary mitogenic actions of prolactin could be dissociated and differentially regulated.

Liver lactogenic factor was found to retain its activity after freezing or lyophilization. In contrast, the activity of liver lactogenic factor was virtually abolished by treatment with HCl (pH 1.0) for 30 minutes followed by neutralization with NaOH (and centrifugation to remove the precipitate). Activity was also lost after treatment at 80° C. for 10 minutes followed by centrifugation of the precipitate. A two-hour incubation with the proteolytic enzyme pepsin was found to destroy liver lactogenic factor activity. The results of these experiments indicated that the factor was a protein or polypeptide.

EXAMPLE 4

THE PRODUCTION OF LIVER LACTOGENIC FACTOR IN VIVO IS DEPENDENT UPON PROLACTIN

As discussed above, liver lactogenic factor (LLF) was associated with states of elevated (lactation) but not basal (virgin female, male) levels of prolactin secretion. This suggested that prolactin may regulate liver lactogenic factor production. In order to determine whether prolactin controlled lactogenic factor production, endogenous prolactin levels were manipulated, and the effect of this manipulation on liver lactogenic factor released was evaluated. Two experimental strategies were used. First, day 10 lactating rats were injected three times at 12-hour intervals with either bromocryptine (BC) (3×2 mg/injection) or inert vehicle and then sacrificed 11 hours after the last treatment. Second, mature male rats were injected daily for seven days with ovine prolactin (0.7 mg/injection) or inert vehicle and killed four hours after the last treatment. In both instances, slices of liver tissue obtained at autopsy were incubated in vitro for three hours, and lactogenic activity of the conditioned medium was tested using the plaque bioassay system described previously. The relative amount of casein released per mammary cell was used as the index of lactogenic activity. Suppression of endogenous prolactin severely attenuated the release of liver lactogenic factor from livers of lactators (100.3±17.0% as compared to 226.4±26.9% of control value for bromocryptine and inert vehicle-injected rats, respectively. Treatment of male rats with ovine prolactin had the opposite effect; liver lactogenic activity rose from undetectable levels (98.9±0.2% of control) in inert vehicle-injected rats to 135.5±12.1% of control after prolactin administration. Since reduction of circulating prolactin diminished hepatic lactogenic activity and injection of prolactin induced such activity, it was concluded that the production of liver lactogenic factor was regulated, in large part, by prolactin.

EXAMPLE 5

LIVER LACTOGENIC FACTOR IS PRESENT IN BLOOD AND CAN MAINTAIN MILK PRODUCTION IN PROLACTIN-SUPPRESSED RATS

To determine whether liver lactogenic factor was present in blood, serum was collected from male and lactating female rats and subjected to an extraction procedure designed to remove prolactin. As a control, prolactin (5 ug/ml) was spiked into both male serum and control medium prior to extraction. After extraction, prolactin-free sera were then diluted in medium and tested in the above-described plaque assay for the presence of a lactogenic factor. The experiment was complicated by the fact that serum PRL levels in both sexes were sufficient to completely overwhelm our bioassay system. This necessitated differential extraction of the serum with acetone; prolactin was precipitated by treatment of serum with 70% acetone and the fraction that precipitated after subsequent exposure to 90% acetone was redissolved and assayed. Male serum treated in this manner was devoid of lactogenic activity as were comparable volumes (3 ml) of male serum spiked with rat prolactin (5 ug/ml) to control for the effectiveness of extraction. In contrast, serum from lactating rats possessed considerable lactogenic activity, indicating that the hepatic lactogen is released by liver tissue into blood.

Prolactin-free serum from lactating female rats contained a factor that significantly increased the average size of casein plaques to 213.3±3.2% of a medium sample extracted concurrently (control). In contrast, extracts of samples of male serum, male serum plus prolactin, and medium plus prolactin produced plaque sizes which were 97.2±3.0, 93.8±3.9, and 79.4±9.6%, respectively, of control values. Thus, serum from lactating rats possessed lactogenic activity which was completely separate from prolactin.

To establish whether liver lactogenic factor could maintain milk production in a prolactin-suppressed rat, lactating female rats (day 10) were treated with either bromocryptine alone or with bromocryptine with a highly enriched preparation of liver lactogenic factor. The rats were injected at 0, 12, and 24 hours, separated from their litters from 10 hours, and then reunited for 30 minutes. The litters of bromocryptine-injected mothers gained 5.02±0.8 g after suckling for 30 minutes, whereas the litters of mothers treated with bromocryptine plus liver lactogenic factor gained 7.07±0.6 g. Thus, liver lactogenic factor significantly augmented milk production in prolactin-suppressed rats. These findings establish the presence of a lactogenic activity in blood which is substantially similar to that produced by liver tissue. Moreover, liver lactogenic factor was found to mimic the lactogenic component of prolactin's actions in vivo as well as in vitro. Thus, these findings indicate that liver lactogenic factor served as an extracellular mediator of prolactin's actions.

EXAMPLE 6

PURIFICATION OF LIVER LACTOGENIC FACTOR

Figure 5:
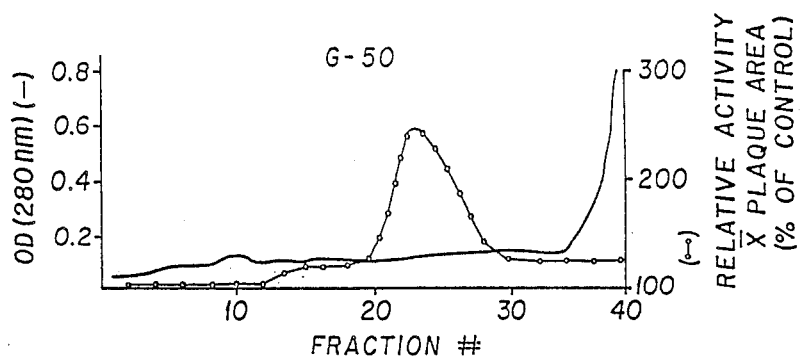
FIG. 5 shows the Sephadex G-50 activity elution profile of liver lactogenic factor.
Figure 6:
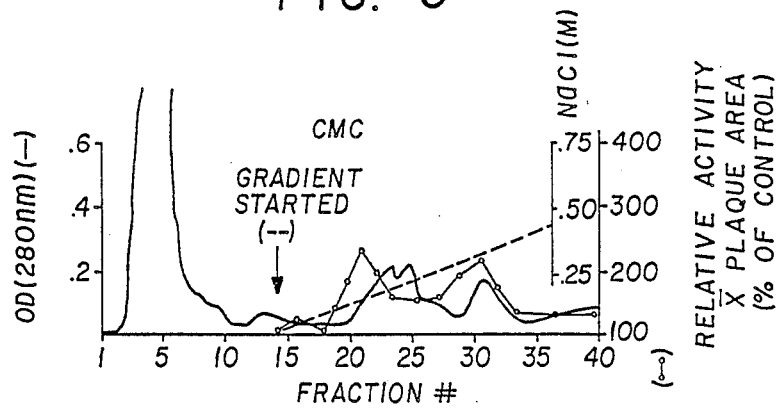
FIG. 6 shows the carboxymethyl cellulose activity elution profile of liver lactogenic factor.
Figure 7:
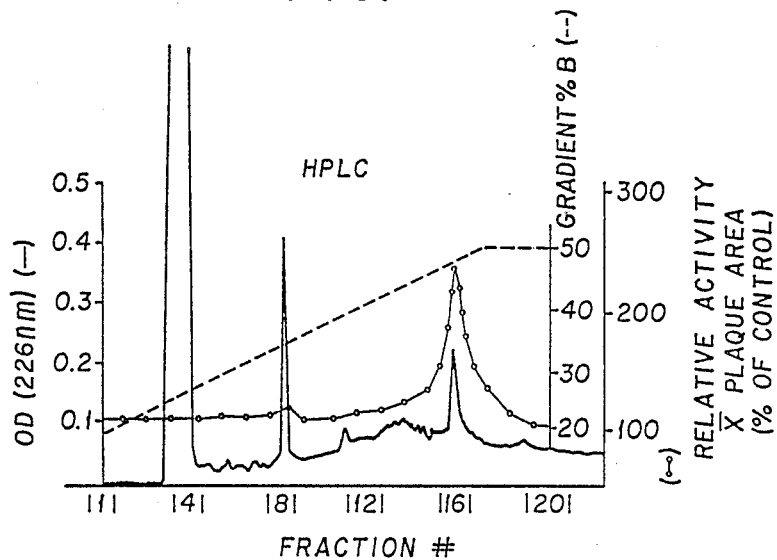
FIG. 7 shows the purification of liver lactogenic factor on a C18 reverse phase HPLC column.

Approximately 8 kg of liver tissue from lactating rats (9-11 days) were suspended in approximately 1000 ml DMEM and homogenized with a polytron (Brinkman). During this procedure, the liver-containing vessel was suspended in an ice bath and, immediately following homogenization, acetone was added to a total concentration of 70%. The extract was maintained at 4° C. overnight whereafter the insoluble pellet was removed by slow-speed centrifugation (4,000 rpm, 15 min). Ice-cold acetone was then added to the supernatant solution to a final concentration of 90%. After two days at 4° C., the supernatant acetone was syphoned off and the pellet was collected, redissolved in double distilled water and lyophilized. Of the resulting 33 g of 90% acetone pellet, 3 g at a time were placed onto a Sephadex G-50 sf column (2.5 cm×40 cm) in 1.0M acetic acid (0.15M NaCl). The effluent of this column was monitored by UV absorption at 280 nm and fractions were collected, pooled, and assayed with the casein plaque bioassay. As seen in FIG. 5, the activity was not associated with a conspicuous protein peak, but its relative position on the column suggests a molecular weight of 8000–10,000 daltons. The active fractions were pooled, lyophilized, and desalted on Sephadex G-25 column in 1.0M acetic acid. A total of 12 mg of the active preparation was then subjected to ion exchange chromatography on a CM cellulose column (1.5 cm×20 cm) and eluted with a gradient consisting of 100 ml 0.05M sodium acetate (pH 5.0) in vessel I and 100 ml 0.5M sodium chloride in vessel II. Two active regions were detected in the effluent of this column as seen in FIG. 6 and both were collected and lyophilized separatey. The final separation on HPLC was done on a C18 reverse phase column, using a gradient of 0.1% trifluoroacetic acid (TFA) in water as solvent A and 0.1% TRA in 80% acetonitrile as solvent B. As seen in FIG. 7, the second activity peak obtained from CM cellulose gave rise to a single peak by HPLC, eluting near the end of the 30-minute linear gradient (from 20% to 50% solvent B). All of the activity was associated with this peak and it was used for subsequent amino acid analyses and physiologic studies.

The results of amino acid analysis of the 24-hour acid hydrolysate of the HPLC bioactive fraction are presented in Table 3. Based on an apparent molecular weight from gel filtration of 8,000 to 10,000 daltons, we conclude the LLF is composed of approximately 85 amino acids (exclusive of tryptophane) and has a molecular weight of approximately 9,400 daltons.

In summary, liver lactogenic factor differs from both native PRL (which has a much greater MW than the lactogen) and the 8,000 MW PRL cleavage product described by Mittra and coworkers (Mittra et al., *Biochem. Biophys. Res. Commun.* 95:1750–1767 (1980)). The basis for this latter conclusion is that the fraction that precipitated between 70% and 90% acetone, which contained extremely high bioactivity, was completely devoid of PRL immunoreactivity when tested in the rat PRL radioimmunoassay distributed by the National Pituitary Agency. This assay employs a polyclonal antibody which most probably recognizes multiple epitopes (including those on the 8,000 MW fragment) of the PRL molecule. The second point is that the lactogen is not insulin-like (i.e., a somatomedin). Its activity is not affected by reduction and alkylation which is consistent with the finding that the molecule does not contain cysteine (Table 3). Moreover, IGF-1 is not active in our casein plaque bioassay system.

TABLE 3

| Amino Acid | Amino acid analysis of LLF | | |
|---|---|---|---|
| | p-moles | Residues | Integer |
| Asp | 429 | 7.8 | 8 |
| Glu | 547 | 9.9 | 10 |
| Ser | 270 | 4.9 | 5 |
| Gly | 402 | 7.3 | 7 |
| His | 94 | 1.7 | 2 |
| Arg | 176 | 3.2 | 3 |
| Thr | 298 | 5.4 | 5 |
| Ala | 399 | 7.2 | 7 |
| Pro | 267 | 4.8 | 5 |
| Tyr | 138 | 2.6 | 3 |
| Val | 282 | 5.1 | 5 |
| Met | 108 | 1.9 | 2 |

TABLE 3-continued

| Amino Acid | Amino acid analysis of LLF | | |
|---|---|---|---|
| | p-moles | Residues | Integer |
| Ile | 115 | 2.1 | 2 |
| Leu | 429 | 7.9 | 8 |
| Phe | 165 | 3.0 | 3 |
| Lys | 565 | 10.3 | 10 |

EXAMPLE 7

PHYSIOLOGIC STUDIEWS OF LIVER LACTOGENIC FACTOR

Figure 8:
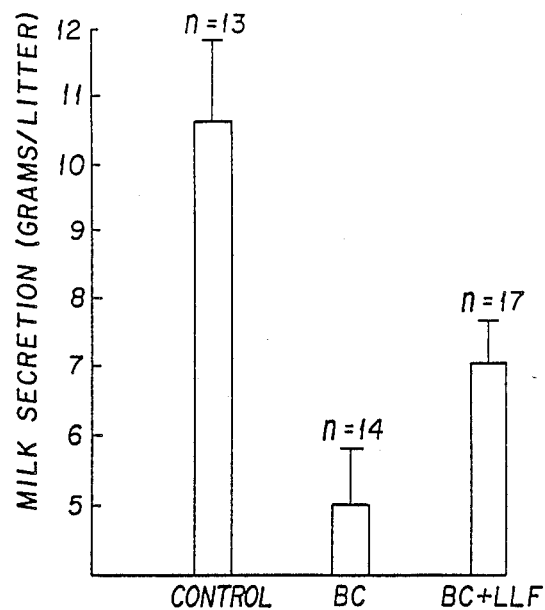
FIG. 8 shows the effect of liver lactogenic factor on milk secretion.

The physiologic relevance of liver lactogenic factor (LLF) on milk production was examined. If LLF mediates the activity of prolactin, then it should influence milk production. Therefore, it follows that is a deficit in milk production was created by suppressing endogenous PRL with bromocriptine (BC), then treatment with liver lactogenic factor should at least partially reverse this deficit. To test this line of reasoning, female lactating rats were treated with either BC alone or BC plus the HPLC purified preparation of liver lactogenic factor (LLF) (a total of 1.5 liver equivalents per animal). The rats were injected at 0, 12, and 24 hours, separated from their litters for 10 hours, and then reunited for 30 minutes. The difference in litter weight measured immediately before and after reuniting the mothers and litters for 30 minutes was used as an index of milk secretion. The data illustrated in FIG. 8 shows that suppression of milk production caused by BC was partially and significantly ($P<0.03$) reversed by concomitant administration of liver lactogen. Thus, this factor can at least partially mimic the actions of prolactin in vivo as well as in vitro.

Figure 9:
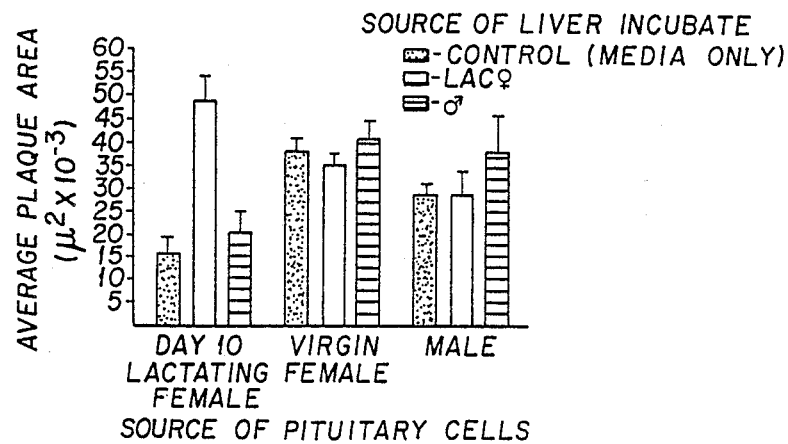
FIG. 9 shows the effect of the source of liver incubate on the amount of casein produced by mammary cells incubated with liver lactogenic factor.

Prolactin (PRL) is viewed as being rather unique among pituitary hormones because its secretion is not controlled via long-loop feedback of an end-organ product. However, the discovery of a PRL-induced substance such as the liver lactogen necessitated a reexamination of this concept. To test the possibility that this hepatic lactogenic factor exerted a direct feedback on PRL-secreting cells, PRL plaque assays on pituitary cells from rats in various endocrine states were run to evaluate the effects of medium conditioned by liver tissue from male and lactating female rats. The results of this experiment are illustrated in FIG. 9. Surprisingly, liver medium from lactating females clearly stimulated rather than inhibited PRL plaque development when pituitary cells derived from lactating females were tested. Incubates of liver tissue from males had no effect on different batches of pituitary cells from the same dispersion. Neither type of liver incubate had any influence on PRL plaque development when pituitary cells from male or virgin female rats were employed. Thus, the sex and physiologic state of an animal appears to influence not only the ability to produce the lactogen but also the capacity of PRL cells to respond to it.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. Liver lactogenic factor having a molecular weight of approximately 8-10 kd and lactogenic peptide fragments thereof in substantially pure form.

2. Liver lactogenic factor in substantially pure form wherein said factor is a protein or polypeptide characterized as follows:
   (a) having a molecular weight of between about 8-10 kd;
   (b) having lactogenic activity which is thermolabile;
   (c) having lactogenic activity which is acid labile;
   (d) having lactogenic activity which is protease sensitive; and
   (e) having lactogenic activity which is not affected by reduction and alkylation.

3. A lactogenic composition which comprises liver lactogenic factor having a molecular weight of approximately 8-10 kd and lactogenic peptide fragments thereof in substantially pure form and a pharmacologically suitable carrier.

4. A method for increasing the production of casein in milk in a lactating mammal which comprises providing to said lactating mammal the liver lactogenic factor of claim 1, in an amount sufficient to increase the production of casein in said milk.

5. A method for increasing the production of casein in milk in a lactating mammal which comprises providing to said lactating mammal the lactogenic composition of claim 3, in an amount sufficient to increase the production of casein in said milk.

6. A method for increasing the production of milk by a lactating mammal which comprises providing to said lactating mammal the liver lactogenic factor of claim 1, in an amount sufficient to increase the production of said milk.

7. A method for increasing the production of milk by a lactating mammal which comprises providing to said lactating mammal the lactogenic composition of claim 3, in an amount sufficient to increase the production of said milk.

* * * * *